United States Patent [19]

Krzeminski

[11] 4,249,525

[45] Feb. 10, 1981

[54] INSTRUMENT FOR LOADING AN INTRAUTERINE DEVICE INTO AN INSERTION TUBE

[75] Inventor: Melvin L. Krzeminski, Palatine, Ill.

[73] Assignee: G. D. Searle & Co., Del.

[21] Appl. No.: 84,702

[22] Filed: Oct. 15, 1979

[51] Int. Cl.³ .............................................. A61F 5/46
[52] U.S. Cl. .................................................... 128/130
[58] Field of Search ........................... 128/127–130, 128/260, 263

[56] References Cited

U.S. PATENT DOCUMENTS

| | | | |
|---|---|---|---|
| 3,398,737 | 8/1968 | Sheppard et al. | 128/130 |
| 3,516,403 | 6/1970 | Cournut | 128/130 |
| 3,777,748 | 12/1973 | Abramson | 128/130 |
| 3,880,156 | 4/1975 | Hoff | 128/130 |
| 3,918,444 | 11/1975 | Hoff et al. | 128/130 |
| 3,918,445 | 11/1975 | Okamoto et al. | 128/130 |
| 4,026,281 | 5/1977 | Mayberry et al. | 128/130 |

Primary Examiner—Lawrence W. Trapp
Attorney, Agent, or Firm—James R. Henes

[57] ABSTRACT

An instrument adapted for collapsing the extended arms of a T-shaped intrauterine device and loading the collapsed device into an insertion tube is disclosed.

4 Claims, 8 Drawing Figures

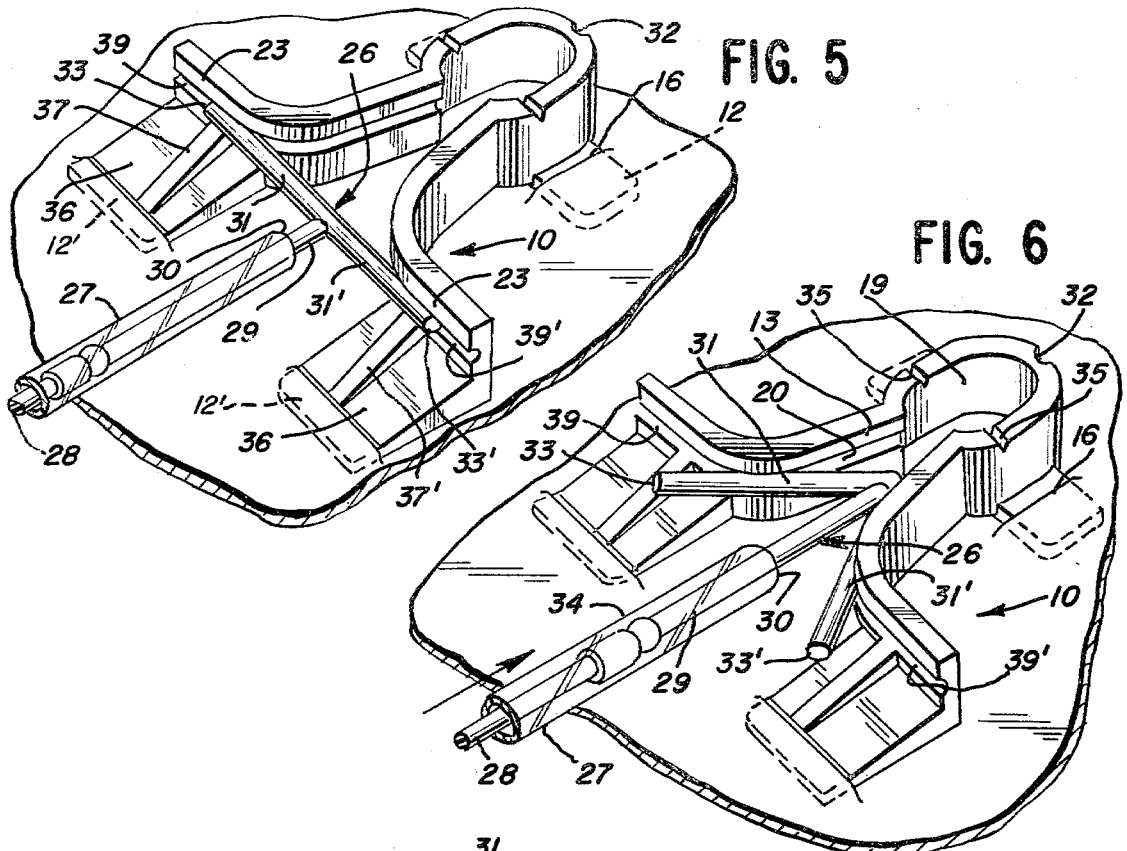
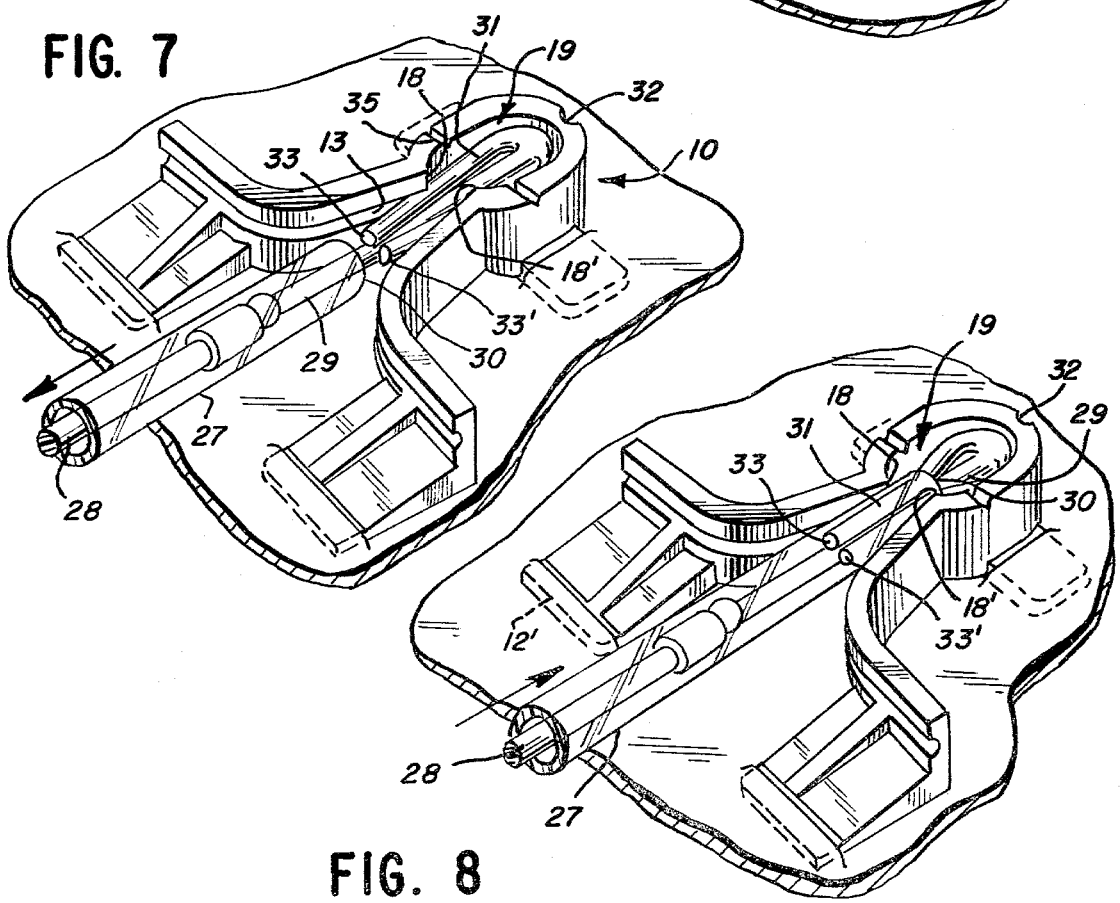

INSTRUMENT FOR LOADING AN INTRAUTERINE DEVICE INTO AN INSERTION TUBE

BACKGROUND OF THE INVENTION

1. Field of the Invention

This invention related generally to an aid for loading an intrauterine device into a tube for insertion into a mammalian uterus and more particularly concerns a mechanical aid for folding the ends of the flexible cross bar of a T-shaped intrauterine device and loading the folded device into an insertion tube.

2. Description of the Prior Art

The "Tatum T" is a T-shaped intrauterine contraceptive device comprising a stem member and a flexible cross bar or arm members integrally attached to and depending generally outwardly from one end of the stem member. Conventionally the Tatum T device is emplaced in the uterine cavity by means of an inserter which consists of an elongated tube adapted to extend through the cervical os and into the uterine cavity. When the insertion tube is loaded with the Tatum T for insertion, the intrauterine device, with the extended arms of the T pressed down along the stem, is positioned in one end of the insertion tube. Then the end of the insertion tube which is loaded with the Tatum T is inserted into the uterine cavity via the vagina and cervix, and the device is then moved from the insertion tube by means of an insertion rod or plunger which extends through the insertion tube and abuts the Tatum T. Holding the insertion rod in place, the insertion tube is withdrawn, thereby permitting the Tatum T to be removed from the insertion tube and the folded arms of the T to unfold and leaving the unfolded T in place in the uterine cavity. The insertion rod and tube are then removed via the vagina and cervix.

The Tatum T intrauterine device is designed to occupy a significant portion of the space in the uterus and therefore is of effective dimensions which are often larger than the cervical os through which it must pass. Thus, insertion of the Tatum T is carried out by use of an insertion tube which modifies the T shaped configuration during insertion. Due to the high elastic memory of the material from which a Tatum T device is generally constructed, it is contemplated that on release in the uterus the device will assume its original T-shaped configuration. However, if force is applied to the Tatum T for an extended time, the configuration assumed while the force has been applied is retained. If the Tatum T fails to assume its T-shaped configuration in the uterus, its effectiveness is impaired. For this reason, it is undesirable to pre-position the Tatum T in its folded insertion configuration for an extended period of time. Rather the Tatum T is restrained in its folded configuration for only a brief few moments immediately prior to use, thereby causing little or no permanent distortion or impairment of the Tatum T.

Thus, when it is desired to insert the Tatum T, the physician at that time fits the extended arms of the T into one end of the insertion tube with his fingers. Manual placement of the Tatum T in the insertion tube is disadvantageous because it is cumbersome and time consuming.

For this reason numerous mechanical devices to facilitate the proper loading of a Tatum T device in an insertion tube have been disclosed. However, only one, the adaptor of Cournut, U.S. Pat. No. 3,516,403, is known which, like the instrument of the present invention is separate from the insertion tube and thus is not inserted with the insertion tube and, if desired, lends itself to repeated use. Cournut's adapter is designed for use solely with an intrauterine device having a specific configuration totally different from that of a Tatum T device.

OBJECT OF THE INVENTION

It is therefore a general object of the present invention to provide an improved instrument for loading an insertion tube with a Tatum T intrauterine device which solves the aforementioned problems.

More particularly, it is an object of this invention to provide an improved instrument for loading an intrauterine device of the T type into an insertion tube which eliminates the need for cumbersome, time consuming handling of the device.

Another object of the present invention is to provide an improved instrument for rapidly and facilely both folding an intrauterine device having substantially transverse arms into a compact configuration and loading the folded device into an insertion tube whereby the folding can be carried out immediately prior to insertion into the uterus thereby avoiding distortion of the intrauterine device caused by long-term prefolding.

It is a further object to provide an improved instrument which can be employed to precisely position a folded T-shaped intrauterine device in one end of an insertion tube such that a predetermined length of the folded tip of the intrauterine device protrudes beyond the end of the insertion tube to facilitate positioning the device at a predetermined location in the uterus.

Other objects and advantages of the invention will become apparent upon reading the following detailed description and appended claims and upon reference to the accompanying drawings.

SUMMARY OF THE INVENTION

The apparatus of this invention is adapted for use with a T-shaped intrauterine device having a stem and flexible arms integrally attached to and depending generally outwardly from one end of the stem and a hollow tube carrying the T-shaped device in one of its ends, with the stem mounted in the end and the arms seated on the end and extending outwardly therefrom. The present invention is an instrument for folding the arms of the T-shaped device toward the stem and loading the stem and folded arms into the aforesaid end of the hollow tube so that the free ends of the folded arms are encompassed within the tube and a predetemined length of the stem and folded arms protrudes therefrom.

The instrument of this invention includes a body having a channel having opposing side walls and a back wall therebetween and being so formed as to be adapted to receive the end of the tube carrying the T-shaped device when the tube is introduced lengthwise and with such end frontwise into the channel between its opposing side walls and towards its back wall. The channel tapers towards its back wall so that its opposing side walls are adapted to exert force on the flexible arms and thereby progressively fold the arms such that the free ends of the arms are fully folded when the T-shaped device carried in the tube is brought into abutment with the back wall of the channel.

Means are included which are adapted for guiding the arms as they are being folded so that when fully folded both arms extend along the length of the stem. Means are also included at a first predetermined distance from the back wall less than the length of the arms, which means are adapted for applying a restraining force to the folded arms and to thereby restrain thereat the stem and folded arms so that, after the T-shaped device in the hollow tube is brought into contact with the back wall of channel and the tube is thereafter withdrawn lengthwise from the back wall to a distance greater than the first predetermined distance, a length of the stem and arms equal to the first predetermened distance is restrained between the restraining means and the back wall. Means are also included for reducing the force applied by the restraining means so that the tube and T-shaped device in the tube can be brought past the first predetermined distance toward the back wall of the channel.

This invention also includes means adapted for biasing the fully folded arms so that, when the folded T-shaped device in the hollow tube is brought into contact with the back wall and thereafter the tube is withdrawn lengthwise from the back wall to a distance therefrom greater than the length of the arms, the free ends of the arms are directed towards each other to a sufficient extent to be encompassed by the hollow tube when the tube is next moved lengthwise toward the back wall to a second predetermined distance therefrom less than the first predetermined distance, leaving a predetermined length, equal to the second predetermined distance, of the stem and arms protruding from the end of the tube.

BRIEF DESCRIPTION OF THE DRAWINGS

For a more complete understanding of this invention reference should now be made to the embodiment illustrated in greater detail in the accompanying drawings and described below by way of an example of the invention. In the drawings:

FIG. 5 is a fragmentary perspective view illustrating an insertion tube, insertion rod therein and an uncollapsed Tatum T carried in one end thereof, aligned for introduction into the loading aid of FIG. 1.

FIG. 6 is a fragmentary perspective view illustrating the use of the loading aid shown in FIG. 1 to fold a T-shaped intrauterine device pre-loaded and carried in an insertion tube as the device and tube are being introduced into the loading aid in the direction of the arrow.

FIG. 7 is a fragmentary perspective view illustrating retraction of the insertion tube in the direction of the arrow and restraint of the fully folded T-shaped intrauterine device in the embodiment of FIG. 1 after having brought the intrauterine device into contact with the end wall of the channel of the loading aid.

FIG. 8 is a fragmentary perspective view illustrating introduction of the insertion tube in the direction of the arrow and encompassing within the insertion tube the free ends and a predetermined length of the intrauterine device restrained in the embodiment of FIG. 1

It should be understood that the drawings are not necessarily to scale. In certain instances, details which are not necessary for an understanding of the present invention or which render other details difficult to perceive may have been omitted. It should be understood, of course, that the invention is not necessarily limited to the particular embodiment illustrated therein.

DETAILED DESCRIPTION OF THE DRAWINGS INCLUDING PREFERRED EMBODIMENTS

Figure 1:
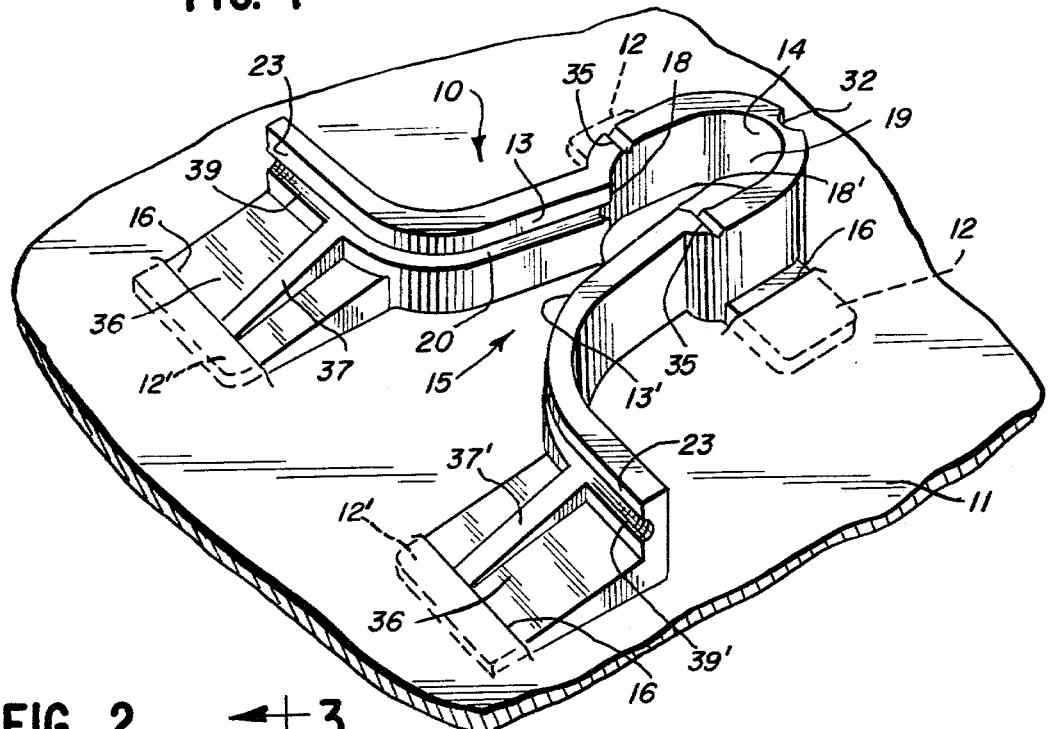
FIG. 1 is a fragmentary perspective view of one embodiment of the insertion tube loading aid of this invention.
Figure 2:
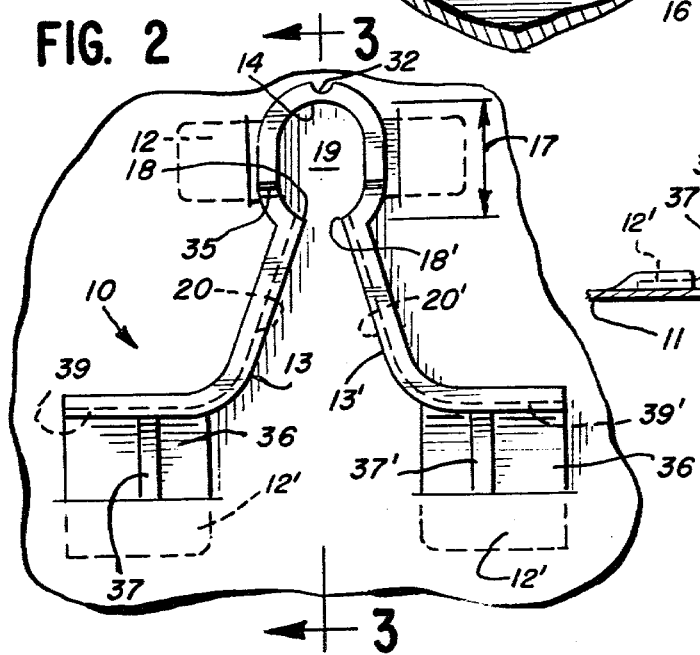
FIG. 2 is a fragmentary top view of the embodiment in FIG. 1.
Figure 3:
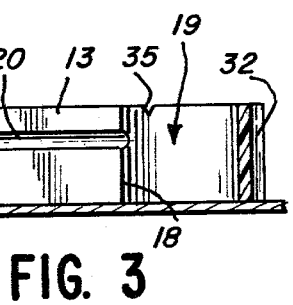
FIG. 3 is a fragmentary view in cross section taken along 3—3 of FIG. 2.
Figure 4:
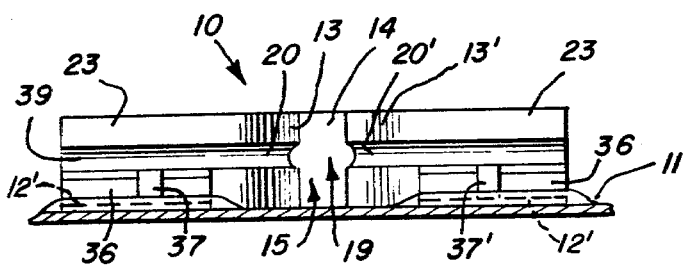
FIG. 4 is a fragmentary front view of the embodment in FIG. 1.

Referring to FIGS. 1-4 together, the improved loading aid of the present invention comprises a body 10 made from any convenient sterilizable material, for example, thermoplastic materials such as polypropylene or polyethylene. The body 10 can be packaged and stored as affixed by any convenient suitable means to a support surface such as a support card 11 and maintained in a sterile environment in a plastic bag (not shown) or under a plastic sheet (not shown) sealed to the support card 11. Further, the body 10 can be marketed as a single unit or in combination with a Tatum T intrauterine device and insertion tube and insertion rod or plunger therefor, possibly also mounted on the support card 11. Suitably hold down tabs 12, $12^1$ on the body 10 are inserted through slots 16 in the support card 11 to affix the body 10 to the card 11. The support card provides a convenient work surface and also serves to maintain the body 10 in the positions shown in FIGS. 1-8.

In the body 10 are formed opposing side walls 13, $13^1$ and end wall 14 to create therebetween a channel 15 which is symmetrical about a substantially vertical plane. The opposing walls 13, $13^1$ converge toward the end wall 14 of the channel 15 to a first predetermined distance 17 from the endwall 14 at which point the wall 13, $13^1$ diverge creating edges 18, $18^1$ which serve as detents as will be described hereinafter. The side walls 13, $13^1$ converge again to ultimately join the endwall 14, to thereby form between sidewalls 13, $13^1$ and the endwall 14 an oval region 19 in the channel 15. The predetermined distance between the endwall 14 and the edges 18 $18^1$ is selected to be less than the length of the arms of the Tatum T. In addition, parallel grooves 20, $20^1$ are formed in the side walls 13, $13^1$, respectively, leading from the surface 23 of the body 10 at the outermost region of the channel 15 to the edges 18, $18^1$, respectively.

FIGS. 5-8 illustrate the loading aid of this invention being used to load a Tatum T into an insertion tube. In practice the Tatum T 26, insertion tube 27 and insertion rod 28 are either supplied to the physician as a unit with the Tatum T 26 pre-loaded in its unfolded or uncompressed configuration in the insertion tube 27 as shown in FIG. 5 or can be so arranged by the physician. In this pre-loaded state the stem 29 is mounted in one end 30 of the insertion tube 27 and the arms 31, $31^1$ are seated on the end 30 and extended outwardly therefrom, as shown in FIG. 5.

In loading the Tatum T 26 in its compressed configuration into the insertion tube 27, the physician, without touching the end 30 of the insertion tube or the pre-loaded unfolded Tatum T 26, can maneuver the end 30 and uncompressed Tatum T 26 pre-loaded therein into alignment with the channel 15, so that the arms 31, $31^1$ are positioned for entry into the grooves 20, $20^1$, respectively, when the tube 27 is introduced lengthwise, and with the end 30 front forward into the channel 15 substantially horizontally and toward the endwall 14 in the direction of the arrow in FIG. 5 along a vertical plane dividing the channel 15 into symmetrical halves. When so introduced, the converging walls 13, 13¹ exert pressure against the arms 31, 31¹ thereby causing the arms 31, 31¹ to collapse to an increasing extent as the insertion tube 27 is being introduced as shown in FIG. 6.

In addition when the tube 27 is first introduced into the channel 15, the arms 31, 31¹ enter the grooves 20, 20¹, respectively. The grooves 20, 20¹ are sized to receive the arms 31, 31¹, respectively, and serve to guide the collapsing arms 31, 31¹ toward the insertion tube 27 as illustrated in FIG. 6.

The maximum pressure exerted on the arms 31, 31¹ by walls 13, 13¹ is at the edges 18, 18¹. The width of the channel 15 between the edges 18, 18¹ is sized to permit the introduction therethrough of the insertion tube 27 and collasping arms 31, 31¹. To reduce resistance at the edges 18, 18¹ to the movement of the tube 27 and Tatum T through the edges 18, 18¹ toward the endwall 14, a notch 32 is provided in the endwall 14 which relieves the pressure in the endwall 14 thereby permitting the edges 18, 18¹ to spring apart when the tube 27 or tube 27 carrying the Tatum T 26 is moved towards the endwall 14 through the 18, 18¹. Turning to FIG. 7, when the end 30 of the insertion tube 27 and arms 31, 31¹ protruding therefrom are introduced into the channel 15 to the maximum extent possible, the folded Tatum T 26 is in abutment with the end wall 14 which serves as a stop presenting further entry of the insertion tube 27 into the channel 15. At that time, the arms 31, 31¹ are folded to the maximum extent desired and the free ends thereof 33, 33¹ are in contact with the insertion tube 27 and preferably with each other.

The insertion tube 27 is next moved in the reverse direction away from the end wall 14 to a point beyond the free ends 33, 33¹ of the folded arms 31, 31¹. During this movement, the folded Tatum T 26 is held firmly in abutment with the end wall 14 by the edges 18, 18¹ which thereby serves as detents gripping the folded arms 31, 31¹ of the Tatum T 26. Thus the width of the channel 15 between the edges 18, 18¹ is also sized to permit retention thereat of the folded arms 31, 31¹ by the edges 18, 18¹ when the insertion tube 27 is moved away from the wall 14.

The oval region 19 between the edges 18, 18¹ and the end wall 14 serves to reduce the pressure on the restrained Tatum T 26 and arms 31, 31¹, thereby minimizing distortion of the folded arms 31, 31¹ and permitting the restrained folded arms to form an arc therein with their free ends 33, 33¹ directed toward each other such that the ends 33, 31¹ are close enough to each other to be encompassed within the insertion tube 27.

When the insertion tube 27 is then moved towards the end wall 14 and over the ends 33, 33¹ of the arms 31, 31¹ and is moved between the edges 18, 18¹ to a second predetermined distance from the end wall 14, a predetermined length of the folded Tatum T which is equal to this second predetermined distance is left protruding from the end 30 of the insertion tube 27. Generally it has been found that, for a Tatum T having a particular set of dimensions, if a particular predetermined length of the unloaded folded Tatum T protrudes from the insertion end 30 of the insertion tube 27, the folded Tatum 26 can be securely loaded in the insertion tube 27 and yet dislodged therefrom in the uterine cavity with a minimum of force. This can be facilitated by incorporating into the body 10 indicia 35 at the second predetermined distance from end wall 14 to which the insertion tube 27 encompassing the folded arms 31, 31¹ should be brought in order to leave protruding from the tube 27 the desired predetermined length of the folded Tatum T 26. Alternatively, indicia can be positioned elsewhere on the body 10 which can be used in conjunction with indicia on the insertion tube 27 to indicate when the insertion tube 27 has reached the second predetermined distance from the end wall 14.

In preferred embodiments, means are provided so that the insertion tube 27 and uncollapsed Tatum T 26 preloaded and carried in the end 30 are brought into alignment with the channel 15 so that upon insertion thereinto the arms 31, 31¹ automatically enter the grooves 20, 20¹. Suitable means for so aligning the Tatum T 26 and insertion tube 27 are illustrated in FIG. 5 and include a ramp 36 having ribs 37, 37¹ thereon extending upward from the tabs 12¹ of the body 10 to a pair of grooves 39, 39¹ on the surface 23 of the body 10 which lead into the grooves 20, 20¹ in the channel 15. Merely sliding the uncollapsed Tatum T 26 pre-loaded into the end 30 of the insertion tube 27 along the ramp 36 and ribs 37, 37¹ and guiding the arms 31, 31¹ into the grooves 39, 39¹ ensures that the arms 31, 31¹ will enter the grooves 20, 20¹ when the pre-loaded Tatum T 26 is introduced into the channel 15.

The insertion tube 27 having a predetermined length of the folded Tatum T 26 loaded in the end 30 can be separated from the body 10 simply by applying a slight force to the insertion tube 27 to lift it upward and free it from between the edges 18, 18¹. The insertion tube 27 is then properly loaded for insertion of the Tatum T 26 into the uterine cavity.

For a Tatum T having a stem of about 1.42 inches in length and arms each of about 0.61 inch in length and a stem and arms of about 0.060 inch in diameter and an insertion tube having inside and outside diameters of about 0.146 and 0.173 inch, respectively, a loading aid having the following approximate dimensions has been suitable: a first predetermined distance 17—that is the maximum length of the oval region 19—of 0.32 inch; the maximum width of the oval region 19 of 0.23 inch; indicia 35 at a distance of 0.25 inch from the back wall 14; a channel width of 0.12 inch between the edges 18, 18¹; a channel width of 0.5 inch at the surface 23; a channel length from the surface 23 to the edges 18, 18¹ of 0.49 inch; and grooves 20, 20¹ of a radius of 0.03 inch.

From the above description it is apparent that the objects of the present invention have been achieved. While only certain embodiments have been set forth, alternative embodiments and various modifications will be apparent from the above description to those skilled in the art. For example, the grooves 20, 20¹ can be replaced by any convenient means for similarly guiding the collapsing arms 31, 31¹ such as ridges on the walls 13, 13¹. These and other alternatives are considered equivalents and within the spirit and scope of the present invention.

Having described the invention, what is claimed is:

1. Adapted for use with a T-shaped intrauterine device having a stem member and flexible arm members integrally attached to and depending generally outwardly from one end of said stem member and a hollow tube carrying said T-shaped device in one end thereof, said stem member being mounted in said end of said tube and said arm members seated on said end of said tube and extending outwardly therefrom, an instrument for folding said arm members toward said stem member and loading said stem member and folded arm members into said end of said tube so that the free ends of said folded arm members are encompassed by said tube and a predetermined length of said stem member and foled arm members protrudes therefrom, said instrument comprising:

a body having a channel having opposing side walls and a back wall therebetween and being so formed in said body as to be adapted to receive said end of said tube carrying said T-shaped device when said tube is introduced lengthwise and with said end frontwise into said channel between said opposing side walls and toward said back wall of said channel, said channel tapering toward said back wall so that said opposing side walls are adapted to exert force on said arm members as said end of said tube carrying said device approaches said back wall such that the free ends of said arm members are fully folded when said device carried in said tube is brought to abutment with said back wall;

means adapted for guiding said arm members as they are being folded so that when fully folded both of said arm members extend along the length of said stem member;

means at a first predetermind distance from said back wall; less than the length of said arm members, which means are adapted for applying a restraining force to said folded arm members and to thereby restrain thereat said stem member and folded arm members so that, after said device in said tube is brought into contact with said back wall and said tube is thereafter withdrawn lengthwise from said backwall to a distance greater than said first predetermined distance, a length of said stem member and said arm members equal to said first predetermined distance is restrained between said restraining means and said backwall;

means adapted for reducing the force applied by said restraining means so that said tube and said device carried in said tube can be brought past said first predetermined distance toward said back wall; and means adapted for biasing said fully folded arms so that, after said device in said tube is brought into contact with said back wall and thereafter said tube is withdrawn lengthwise from said back wall to a distance therefrom greater than the length of said arm members, said free ends are directed towards each other to a sufficient extent to be encompassed by said tube when said tube is next moved lengthwise towards the back wall to a second predetermined distance threfrom, less than said first predetermined distance, leaving a predetermined length of said stem member and arm members protruding from said end of said tube, said predetermined length being equal to said second predetermined distance.

2. The instrument of claim 1 comprising additionally indicia on said body indicating said second predetermined distance from said back wall to which said tube is moved.

3. The instrument of claim 2 wherein said indicia is a marking on said body at said second predetermined distance.

4. The instrument of claim 1 comprising additionally means adapted for aligning said tube carrying said T-shaped device for introduction into said channel so that said arm members are positioned so as to be acted upon by said guiding means upon introduction thereinto.

* * * * *